United States Patent [19]
Metz et al.

[11] Patent Number: 5,974,162
[45] Date of Patent: Oct. 26, 1999

[54] DEVICE FOR FORMING AND DETECTING FINGERPRINT IMAGES WITH VALLEY AND RIDGE STRUCTURE

[75] Inventors: Michael Metz, Yorktown Heights; Carl Flatow, Oceanside, both of N.Y.; Nicholas J. Phillips, Loughborough, United Kingdom; Zane Coleman, Mableton, Ga.

[73] Assignee: ImEdge Technology, Inc., Yorktown Heights, N.Y.

[21] Appl. No.: 08/394,470

[22] Filed: Feb. 27, 1995

Related U.S. Application Data

[63] Continuation-in-part of application No. 08/198,988, Feb. 18, 1994, abandoned.

[51] Int. Cl.$^6$ ...................................................... G06K 9/00
[52] U.S. Cl. .......................... 382/124; 382/125; 382/126; 382/127; 356/71
[58] Field of Search ................................... 382/124, 126, 382/116, 210, 125, 127; 356/71

[56] References Cited

U.S. PATENT DOCUMENTS

| | | | |
|---|---|---|---|
| 3,174,414 | 3/1965 | Myer ............................................. | 95/1.1 |
| 4,340,300 | 7/1982 | Ruell .......................................... | 356/71 |
| 4,728,186 | 3/1988 | Eguchi et al. ............................. | 356/71 |
| 4,905,293 | 2/1990 | Asai et al. ................................ | 382/126 |
| 4,924,085 | 5/1990 | Kato et al. .......................... | 250/227.28 |
| 5,077,803 | 12/1991 | Kato et al. ................................ | 382/124 |
| 5,088,817 | 2/1992 | Igaki et al. ................................ | 356/71 |
| 5,109,427 | 4/1992 | Yang ......................................... | 382/124 |
| 5,177,802 | 1/1993 | Fujimoto .................................. | 382/124 |
| 5,241,606 | 8/1993 | Horie ........................................ | 382/126 |
| 5,448,659 | 9/1995 | Tsutsui et al. ............................ | 382/124 |
| 5,455,693 | 10/1995 | Wreede et al. ............................ | 359/15 |

FOREIGN PATENT DOCUMENTS

WO 94/25938  11/1994  United Kingdom ............. G07C 9/00

OTHER PUBLICATIONS

Planar–Optic–Disk Pickup with Diffractive Micro–Optics, written by Teruhiro Shiono and Hisahito Ogawa, published by Applied Optics, vol. 33, No. 31, Nov. 1, 1994, 6 pages.

Magic Finger™, brochure, distributed by Information Spectrum, Inc., 2 pages.

FingerCheck FC100, press release published by Startek Engineering, Inc., Taiwan, 7 pages, Apr. 1994.

TouchPrint™, brochure published by Identix, Inc., 1993, 2 pages.

The Direct Fingerprint Reader " . . . The Better Way to Capture the Highest–Quality Finger Images 'Live' for Identification Purposes" by Indenticator Technology, 1993, 3 pages.

Holographic Fingerprint Sensor, written by Shin Eguchi, Seigo Igaki, Fumio Yamagishi, Hiroyuki Ikeda, and Takefumi Inagaki, published by Practical Holography III, SPIE vol. 1051, 1989, 7 pages.

Real–Time Fingerprint Sensor Using a Hologram, written by Seigo Igaki, Shin Eguchi, Fumio Yamagishi, Hiroyuki Ikeda, and Takefumi Inagaki, published by Applied Optics, vol. 31, No. 11, Apr. 10, 1992, 9 pages.

*Primary Examiner*—Jose L. Couso
*Assistant Examiner*—Anh Hong Do
*Attorney, Agent, or Firm*—Hopgood, Calimafde, Kalil & Judlowe

[57] ABSTRACT

A method and ultra-compact system has been developed for illuminating and detecting the surface topography of an object such as the finger of an individual. The system is capable of producing high-contrast images which can be electronically transmitted in real-time, or stored using electronic or photographic recording devices. Light traveling within a light transmitting substrate is redirected by a slanted-fringe light diffractive grating preferably embodied within a volume hologram. The volume hologram, either of the reflection or transmission type, is attached to the light transmitting substrate, and functions to diffract light striking thereupon and illuminate an object having topographical surface structure. After being spatially and intensity modulated in accordance with topographical details of the illuminated object, the modulated light passes back through the light transmitting substrate and the volume hologram, onto an image detection array, for subsequent analysis. Each of the disclosed embodiments has a compact geometry suitable for use in diverse object identification applications.

35 Claims, 8 Drawing Sheets

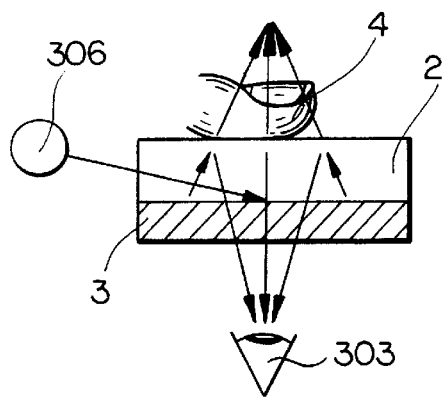
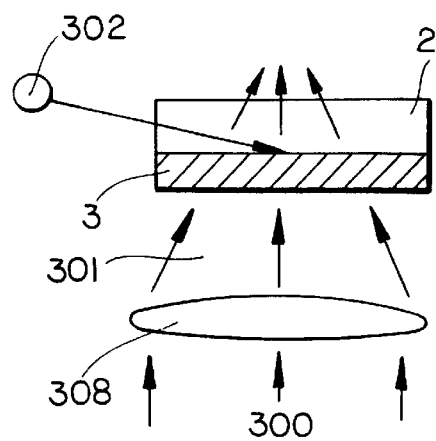
FIG. 11
FIG. 11A
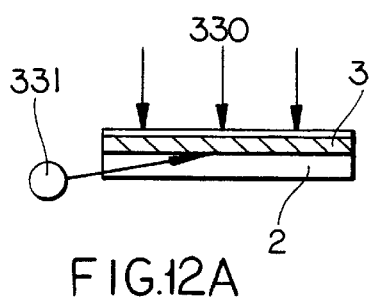
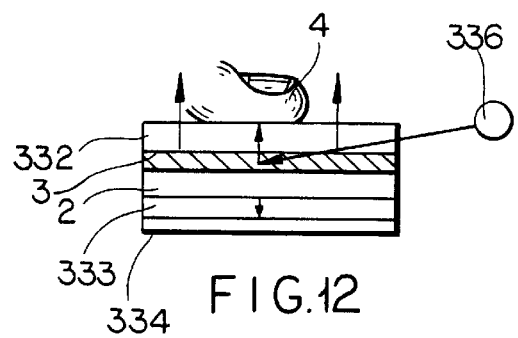
FIG. 12A
FIG. 12
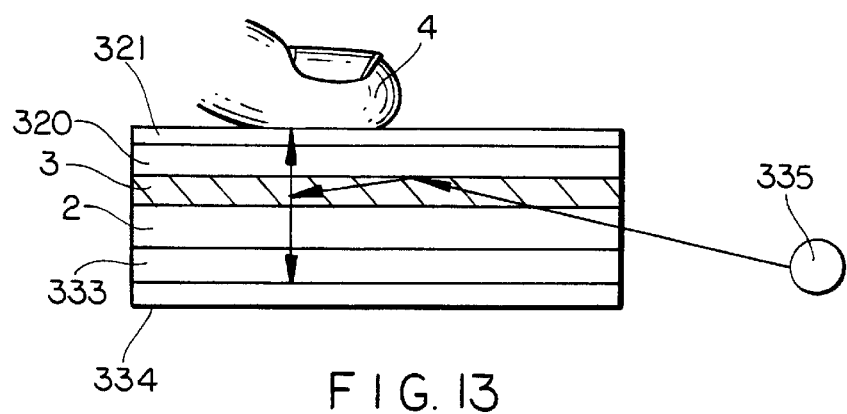
FIG. 13

DEVICE FOR FORMING AND DETECTING FINGERPRINT IMAGES WITH VALLEY AND RIDGE STRUCTURE

RELATED CASES

This is a Continuation-in-Part of application Ser. No. 08/198,988 filed Feb. 18, 1994, now abandoned, incorporated herein by reference.

BACKGROUND OF THE INVENTION

1. Field of the Invention

The present invention relates to a method and apparatus for producing and detecting an image of a topographic surface, such as a fingerprint, for optical viewing or storage in a recording medium such as photographic film, a hologram, or computer storage means. Such topographic images may be analyzed or compared with previously recorded topographic data. Such methods and apparatus are used, for example, for personal identification in the criminology and access control fields.

2. Description of the Related Art

Examination of the fingerprints or other biometric features of an individual is a well known technique to establish a person's identity. In the past, fingerprints were recorded by applying ink to the finger and then rolling the finger on a piece of paper. Agencies then maintained these originals, or photocopies or photographs of the originals. Later comparison of these archives with a live or latent fingerprint could prove to be quite tedious and time consuming. More recently, methods have arisen to create fingerprint images which can be captured directly electronically for storage and/or analysis by a computer, or photographically for storage on film.

Many methods have been proposed for optical detection of fingerprints and other topographic biometric features such as footprints and palmprints. Most of these methods utilize optical systems which typically incorporate a prism or beamsplitting apparatus, and operate on the principle of frustrated total internal reflection. Such systems are necessarily bulky, cannot detect certain skin detail information, such as valley or pore detail, or require expensive optical components. In addition some prior art systems suffer from distortion, poor signal to noise ratio, aberrations, lack of contrast, and/or lack of resolution of finger detail information.

There are many patents which describe optical systems which use prisms to produce illuminating light. In such systems, one side of a prism is illuminated with light, while a subject's finger is pressed against another surface of the prism, usually its hypotenuse. A fingerprint image is formed by frustrated total internal reflection where the finger meets the prism. Light passing out of the prism containing the fingerprint image is then captured by an image detection system. Examples of prism-based finger print detection systems can be found in U.S. Pat. No. 3,174,414 to Myer, U.S. Pat. No. 3,482,498 to L. Becker and U.S. Pat. No. 3,947,128 to Z. Weinberger, et al.

A number of prior art systems have been developed, which illuminate the finger directly without using the principle of total internal reflection. U.S. Pat. No. 5,177,802 to Y. Fujimoto, et al. describes several finger print detection systems which do not use the principle of frustrated total internal reflection. As disclosed therein, one such system uses a light guiding plate having a through hole, so that the finger is in air, and light traveling through the light guide exits the light guide near the hole to illuminate the finger. The finger image is captured by a detection system directly opposite the finger. In another system disclosed in this U.S. Patent, a light guiding substrate is not used, and instead, a pair of linear light sources, such as fluorescent tubes, are placed near the 'belly' of the finger to be imaged, and detection system images the finger directly. This embodiment suffers from bulkiness and direct lamp light reaching the image detector, thus reducing the signal to noise ratio of images produced using this system. In other embodiments, the finger is illuminated directly via light emerging from the light guiding plate. However, in such systems, the light strikes the finger at an angle, limiting uniformity of illumination and contrast.

Various fingerprint detector systems have been developed, using image comparison and illumination scanning techniques. For example, U.S. Pat. No. 3,511,571 describes a system which floods the surface of the finger with light. The light reflected from the finger is passed through a transparency of a previously recorded fingerprint, for direct comparison. The systems disclosed in U.S. Pat. Nos. 3,200,701; 3,864,042; and 4,003,656 scan a light beam across a finger and detect light therefrom in order to produce an output signal for constructing a fingerprint image.

U.S. Pat. No. 3,430,300 to H. Ruell describes a system for forming a latent topographic relief of a finger pattern. This system uses a deformable polymer which is illuminated through its edge, while a finger is pressed thereupon. The deformation of the polymer, due to finger pressure, frustrates total internal reflection of the light, thereby redirecting the illuminating light at the points of frustration to the output face of the substrate.

Various methods have been proposed utilizing holograms as part of the fingerprint illumination and detection system. U.S. Pat. No. 5,109,427 describes a fingerprint recognition device which uses collimated laser light to illuminate a finger through a tetragonal prism. A hologram is used to shift the axis of the fingerprint image to a second optical axis, so that an objective lens can then project the fingerprint image to a CCD camera.

The paper entitled "Real-time fingerprint sensor using a hologram", Applied Optics, Vol. 31, No. 11, p.1794ff, and U.S. Pat. No. 4,728,186 entitled 'Uneven Surface Date Detection Apparatus', each describe a system which uses laser light to illuminate a finger directly using a light guiding substrate. The scattered light reflected from the finger travels through the light guiding substrate and is permitted to exit therefrom through a plain grating-type hologram attached to the substrate. A lens aligned with the plain guiding-type hologram then forms an image of the fingerprint which is subsequently detected by a CCD camera or other detector. U.S. Pat. No. 4,728,186 also discloses a system which uses a hologram to direct the light to the finger. However, in this prior art system, the image travels by total internal reflection towards a hologram which directs the image towards an image detection system located along a different optical axis from the finger. As the input light path to the finger and the output light path to the detection system are necessarily along different optical axes, this prior art system is likely to suffer from (i) loss of information due to imperfections in the waveguide-type light guiding substrate, and/or (ii) damage to the image information (e.g. addition of noise, distortions or aberrations) due to propagation of light rays through the waveguide and/or the light extracting hologram. In addition, the geometry of this prior art system limits its ability to be extremely compact.

Other prior art systems make use of holograms, but for different purposes. For example, in U.S. Pat. No. 4,053,228, a fingerprint is compared against a fingerprint which is stored on a hologram.

Thus, there is a great need in the art for an improved method and apparatus for producing high-contrast images of the surface topography of objects, such as finger and foot surfaces, while avoiding the shortcomings and drawbacks of prior art systems and methodologies.

OBJECTS OF THE PRESENT INVENTION

Accordingly it is a primary object of the present invention to provide a compact device which yields high contrast and high resolution images of the topography of an object, which images contain little or no aberrations or distortions.

A further object of the present invention is to provide a ultra-compact device for detecting and/or recording images of topographical surface structure of objects.

A further object of the present invention is to provide such a device for use with portable computer-based systems.

A further object of the present invention is to provide a system for producing fingerprint images with sufficient detail to differentiate between the ridges and valleys thereof.

A further object of the present invention is to enable high contrast imaging of finger pores and/or valley artifacts.

A further object of the present invention is to provide such a device for biometric identification applications.

A further object of the present invention is to provide a novel method of producing and detecting images of topographical surface structure associated with fingerprints.

A further object of the present invention is to provide a novel method of image detection that may be applied to a broad range of objects whose features are desired to be inspected, imaged, detected, recorded, and/or compared to previously recorded object data.

These and other objects of the present invention will become apparent hereinafter and in the claims.

SUMMARY OF THE INVENTION

In accordance with one aspect of the present invention, a novel topographical image detection device is provided. In general, the device comprises a light source, a light transmitting substrate, and a slanted-fringe type light diffractive grating. The light diffractive grating may be embodied within holographic or non-holographic structures having a volumetric extent. The device further includes a planar object illuminating region for illuminating and/or supporting an object, such as a finger, palm, or foot surface, having topographical surface structure. The light produced from the light source enters the light transmitting substrate, travels therethrough, strikes the slanted light diffractive grating at an oblique angle, and is diffracted thereby with substantial efficiency into the first diffraction order of the light diffractive grating. The diffracted light rays travel in the direction of the object illuminating region of the light transmitting substrate. Light is reflected from the substrate/air interface and passes back through the light transmitting substrate, through the slanted light diffractive grating, and can be seen as a glare by a light receiving means, such as an eye, an electronic image detector, or a film recording camera.

When an object, such as a finger, is brought in proximity with the object illuminating region of the device, which may or may not be in contact with the light transmitting substrate in embodiments, the illuminating light rays are absorbed or otherwise scattered from the finger ridges pressed up against object illuminating region. This interrupts the aforementioned light glare and produces a light field containing a high contrast image of the fingerprint. The image is then transferred along the redirected optical axis of the device, through the light transmitting substrate and light diffractive grating, and onto the image detection or recording medium. The image detecting medium may be realized as a system comprising an objective lens and a CCD; an eye; or a film-type camera. Because the finger, the slanted grating and the image detection element (i.e. eye or camera) are disposed along substantially the same optical axis, aberrations and distortion of the fingerprint image are minimized or eliminated. Notably, portions of the finger contacting the object illuminating region of the device appear as dark regions in the produced fingerprint image, whereas non-contacting regions appear as light regions in the fingerprint image.

The geometrical dimensions of the imaging device can be made extremely compact so as to fit within a thin package, such as those typically used for computer PCMCIA cards.

According to another aspect of the present invention, a novel object identification system is provided. A disclosed, the system uses the image detection device hereof in conjunction with a computer-based system for performing image analysis. The system may include image or like databases for use by the image analysis system. As disclosed, the system uses other advantages of the present invention will become apparent hereinafter.

BRIEF DESCRIPTION OF THE DRAWINGS

For a more complete understanding of the Objects of the Present Invention, the following Detailed Description of the Illustrative Embodiments should be read in conjunction with the accompanying Drawings, wherein:

FIG. 11 is schematic diagram of the topographical image detector of the sixth illustrative embodiment of the present invention, in which the light transmitting substrate is arranged to support an object such as a finger, and to which is affixed a volume hologram embodying a slanted-fringe light diffractive grating designed to converge illuminating light rays reflected from the object towards a viewing system, such as the human eye;

FIG. 11A is an optical arrangement for recording the slanted-fringe light diffractive grating in the volume hologram used in the sixth embodiment of the topographical image detector of the present invention shown in FIG. 11;

FIG. 12 is a schematic diagram of the topographical image detector of the seventh illustrative embodiment of the present invention, in which a light transmitting superstrate is arranged to support an object such as a finger, a reflection-type volume hologram embodying a slanted-fringe light diffractive grating is affixed to underside of the light transmitting superstrate, and a light transmitting substrate is affixed to the underside of the volume hologram;

FIG. 12A is an optical arrangement for recording the slanted-fringe light diffractive grating in the volume hologram used in the seventh embodiment of the topographical image detector of the present invention shown in FIG. 12;

FIG. 13 is a schematic diagram of the topographical image detector of the eighth illustrative embodiment of the present invention, in which a reflection-type volume hologram embodying a slanted-fringe light diffractive grating is disposed between an object supporting layer and a light transmitting substrate, and is illuminated from the phase-conjugate direction by virtue of total internal reflection between the reflection-type volume hologram and an index discontinuity layer disposed between the object supporting layer and the reflection-type volume hologram.

DETAILED DESCRIPTION OF THE ILLUSTRATIVE EMBODIMENTS OF THE PRESENT INVENTION

Referring to the figure drawings of FIGS. 1 through 14, the topographical surface imaging and detection system of the present invention will now be described in great detail below.

For purposes of illustration, the illustrative embodiments of the present invention will consider imaging the topographical surface of three-dimensional objects, such as fingers and palms, known as fingerprints and palmprints. However, it is understood that topographical surfaces of other types of objects may be imaged with high contrast and resolution using the method and apparatus of the present invention.

Figure 1:
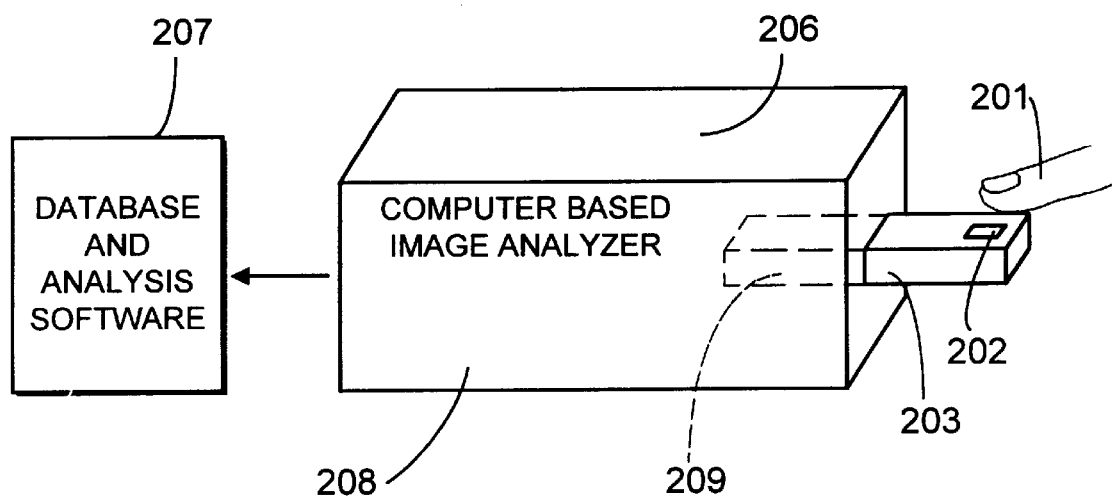
FIG. 1 is a perspective view of a topographical image capture, analysis and storage system of the present invention, showing the various integrated system components thereof, namely its topographical image detection subsystem, computer-based image analyzing subsystem, input/output interface circuitry, and archive image database subsystem.
Figure 2:
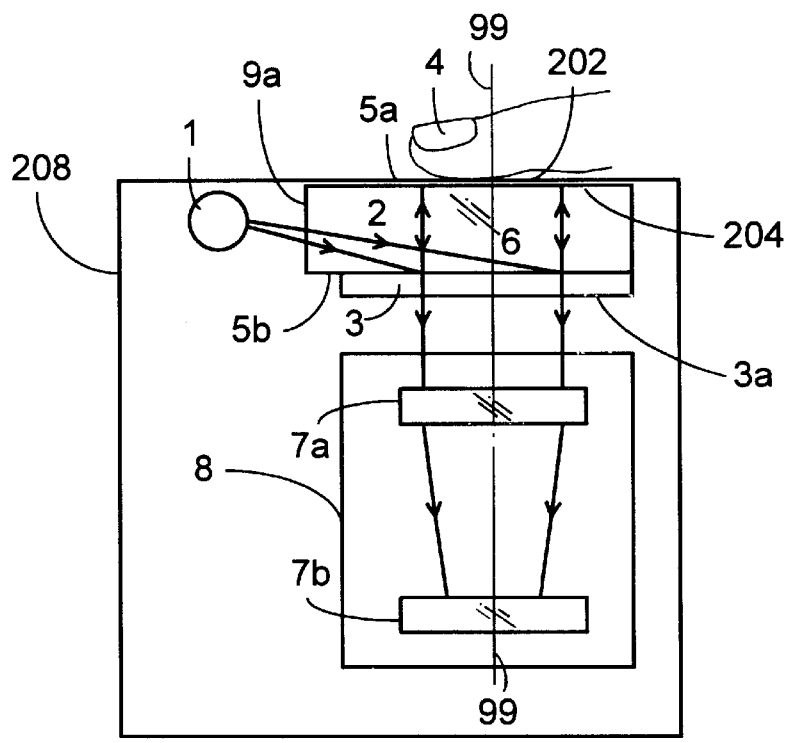
FIG. 2 is schematic diagram of a topographical image detector of the first illustrative embodiment of the present invention, in which a slanted fringe light diffractive grating is coupled to a compact light transmitting substrate in accordance with the principles of the present invention.

As shown in FIG. 1, the topographical surface imaging and detection system of the present invention comprises a number of subcomponents, namely: topographical image detector 203, computer-based image analyzer 206, and archive image database 207. A person uses the system by placing his or her finger 201 through opening 202 formed in imaging system housing 203. Opening 202 provides access to planar object (i.e. finger) illuminating region 204, which is realized as a portion of planar substrate 2, as shown in FIG. 2. Preferably, the fingerprint image is captured by an electronic detector 205, which may be realized as a CCD image detection array located within housing 203. The signal from the detector 205 is electronically fed to computer-based image analyzer 206 within housing 208, by way of input/output (I/O) interface circuitry 209. Notably, housing 208 may be different than housing 203. The pixelized data set corresponding to the detected fingerprint is then stored in computer database 207, for subsequent analysis or comparison. Alternatively, detected fingerprint images may be compared in real-time to previously recorded fingerprint images in database 207 for any diverse number of identification purposes (e.g. criminology, access control etc.). It is understood that the housing 203 and 208 are merely representative and will vary from embodiment to embodiment of the present invention.

FIG. 2 illustrates the structure and function of the first illustrative embodiment of the topographical image detection system of the present invention. As shown, this embodiment of the image detection system comprises a number subcomponents contained in compact housing 208, namely: a light source 1 (e.g. a small tungsten or xenon lamp) with beam reshaping optics, for emitting a light beam; a light transmitting substrate 2, made of an optically transparent material such as acrylic, and having an object illuminating region (i.e. surface); a reflection-type volume hologram 3 embodying a slanted-fringe type light diffractive grating, affixed to the light transmitting substrate; and an image detection system 8 in proximity with light diffractive grating 3, as shown. In the illustrative embodiment, lamp 1 is placed approximately 1–2" from the substrate edge, as shown, to provide an image detector with a highly compact construction image detection system 8. In alternative embodiments, lamp 1 or equivalent light source may be located remotely from the substrate 2, and coupled thereto using fiber optic elements known in the art. In typical applications, light source 1, volume hologram 3, light transmitting substrate 2, and image detection system 8 will be contained in compact housing 203 which includes opening 202 for guiding the physical placement of a finger onto the finger illuminating region of the light transmitting substrate 2.

As shown in FIG. 2., light source 1 is arranged so that light emitted therefrom travels at an oblique angle within substrate 2. This is achieved by illuminating the edge 9a of substrate 2 at a slight angle off the normal to the edge. In the first illustrative embodiment, substrate 2 is bounded by face surfaces 5a and 5b and edge surfaces, 9a, b, c and d. Typically, the face surfaces have a larger surface area than the edge surfaces. During operation of the system, the polished edge of the substrate 2 is lit by tungsten or xenon lamp 1 so as to cause a substantial amount of the input light to fall incident upon the slanted-fringe light diffractive grating within the volume hologram 3. This incident light diffracts into the first diffraction order of the reflection-type volume hologram 3 along optical axis 99 towards the object illuminating region of the substrate. This redirected light illuminates a finger placed on the light transmitting substrate 2, reflects back along the optical axis 99 after having been spatially and intensity modulated by the topographical surface pattern (i.e. valleys and ridges) in the illuminated fingerprint. The reflected light then passes through image forming lens 7A and onto CCD image detector 7B, to produce a high contrast fingerprint image of the illuminated finger.

Figure 3:
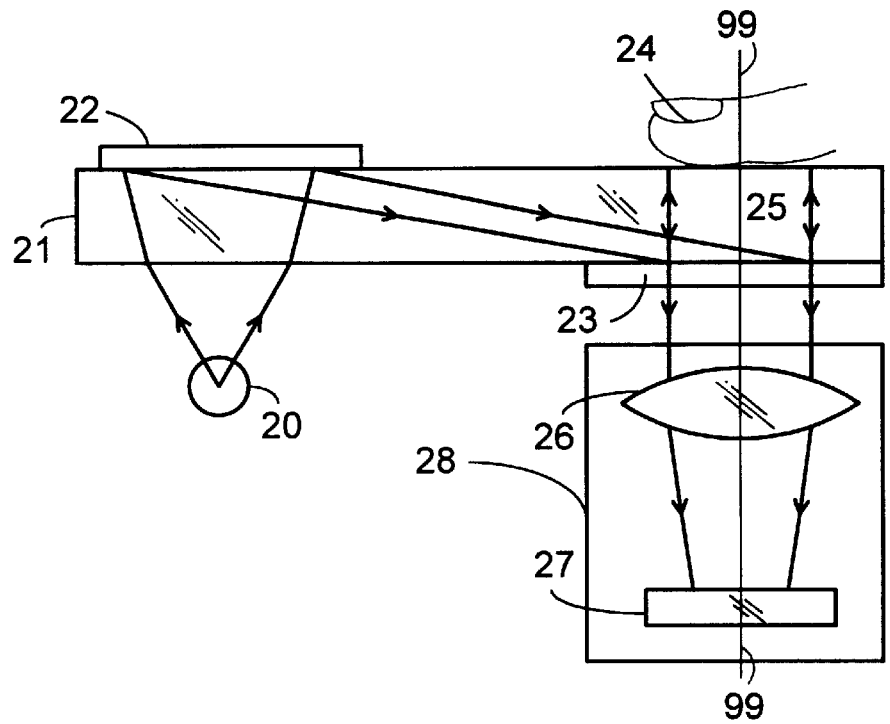
FIG. 3 is schematic diagram of a topographical image detector of the second illustrative embodiment of the present invention, in which a first slanted-fringe light diffractive grating is realized in a volume hologram affixed to a light transmitting substrate at a position along the optical axis of the image detector and object illuminating region of the substrate.
Figure 4:
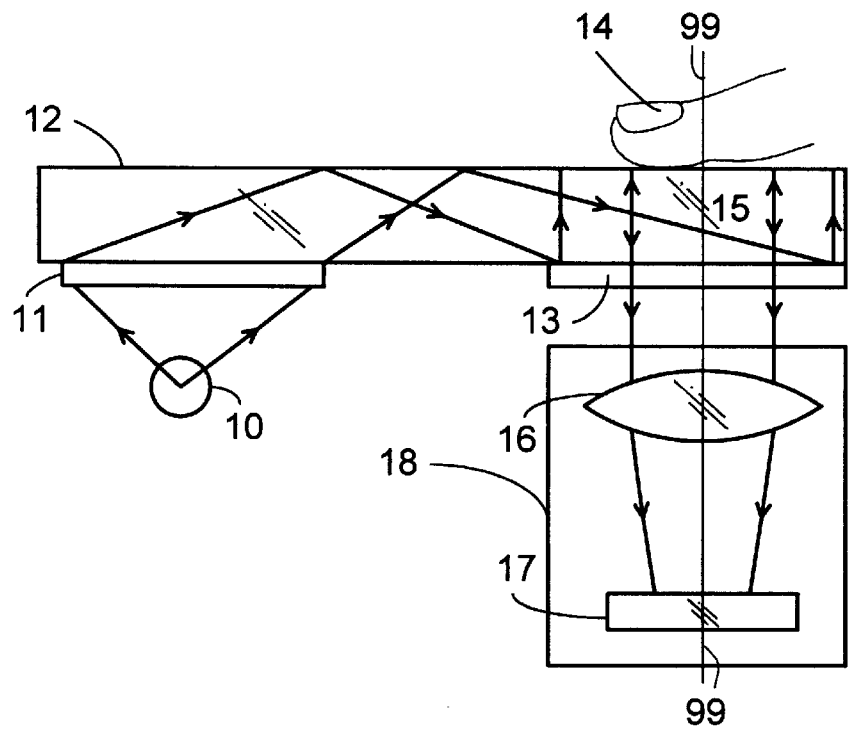
FIG. 4 is schematic diagram of a topographical image detector of the third illustrative embodiment of the present invention, in which illuminating light enters the light transmitting substrate through an input light-coupling hologram attached to the face of the substrate, and is totally internally reflected therewithin before the illuminating light illuminates the output light-coupling hologram, also affixed to the substrate but at a position along the optical axis of the image detector and object illuminating region of the substrate.

If desired or required, alternative means may be used to cause light emitted from light source 1 to enter light transmitting substrate 2 and travel therewithin at an oblique angle directly towards the slanted-fringe light diffractive grating, as shown in FIG. 2. For example, the edge 9a of the light transmitting substrate 2 may be beveled in order to change the angle of entry of the light beam from light source 1. Alternatively, the light may be forced to enter the light transmitting substrate by way of face surfaces 5a or 5b. As shown in FIGS. 3 and 4, this can be achieved using, for example, a prism, a light diffraction grating, or a hologram separate and apart from volume hologram 3.

As shown, volume hologram 3 can be laminated to face surface 5b of substrate 2 either directly, or indirectly by way an additional intermediate layer or fluid or adhesive means that matches the indices of refraction between the light transmitting substrate 2 and the volume hologram 3. In the illustrative embodiment, hologram 3 comprises a recording medium embodying a previously recorded volume slanted-fringe grating structure. Suitable recording media include, but are not limited to, DuPont holographic recording photopolymer, silver halide recording materials, dichromated gelatin, Polaroid DMP-128 photopolymer, etc. While holographic techniques have been used to realize the slanted light diffractive gratings used in the devices of the present invention, it is understood that other non-holographic techniques and materials may be used for producing a slanted-fringe light diffractive grating structure of acceptable definition for use in the present invention. Optionally, the recording medium of volume hologram 3 may be protected by a cover 3a composed of a transparent material. This material may be flexible, such as, for example, Mylar, or a more rigid material such as a plastic such as acrylic or polycarbonate, or glass.

In general, image detection system 8 comprises an image transfer means 7A, and an image detection means 7b. The image transfer means 7A may be realized as any device capable of transferring the image produced by the finger on surface 5a, onto the surface of the image detector 7b. Suitable devices for realizing the image transfer means 7A include the lens of an observer's eye, a lens or lens system, a lenslet array, a fiber optic array, a microchannel plate, or any combination thereof. Suitable devices for realizing the image detection means 7B include the retinal surface of an viewer's eye, a CCD image detection array, a CMOS image detection array, a photographic film structure, or any other suitable image capture means. As shown in FIG. 2, the object illuminating region, the volume hologram 3, the image transfer means 7A and the image detection means 7B are disposed about optical axis 99.

Referring to FIG. 2, the physical operation of the image detection device of the first illustrative embodiment shall be described in greater detail below.

In general, light produced from light source 1 may be diverging, converging, collimated or otherwise anamorphically reshaped, depending on the enabling technology used and the product application. The produced light rays travel at an oblique angle directly through the light transmitting substrate 2, as shown in FIG. 2, to strike the slanted-fringe light diffractive grating embodied within volume hologram 3. The slanted light diffractive grating diffracts a substantial portion of the light impinging on it into the first diffracted order, according to the well known Bragg condition $$\lambda = 2d \sin\theta$$

where $\lambda$ is the illumination wavelength of the light source 1, d is the grating fringe spacing of the volume hologram, and $\theta$ is the half angle between the object beam and the reference (or reconstruction) beam. A detailed explanation of the Bragg condition and the recording and playback of holograms and the associated well known terminology used in holography such as object, reference and reconstruction beams can be found in any of numerous books on holography, such as Practical Holography, second ed., by G. Saxby, Prentice Hall, 1994.

The light diffracted into the first diffraction order from volume hologram 3 is redirected to travel in the direction of optical axis 99, and through object illuminating region 6. The angle at which these first order diffracted light rays travel is referenced with respect to the face 5a of light transmitting substrate 2 and is less than the critical angle of the substrate 2, the optical axis of which typically approaches or is approximately normal thereto, as shown in FIG. 2. Depending on the requirements of the specific application, the light diffracted from the volume hologram may be collimated, converging, or diverging, as long as the extreme light rays travel at an angle less than the critical angle for the light transmitting substrate 2.

When a finger 4 is placed through opening 202 in housing 203 and pressed onto the planar object illuminating region 204 of face 5a of substrate 2 within the boundaries of region 6 containing the diffracted light field, the ridges and other details of finger 4 interrupt the glare field and absorb or scatter incident light, producing a high contrast fingerprint image. If the ridges of the finger are slightly sweaty or greasy, better "index matching" to the substrate 2 will occur, producing a higher contrast fingerprint image. For dry or low contrast fingers, a small amount of grease from a nose, forehead, or a substance like petroleum jelly may be used on the finger to improve contact contrast. The fingerprint image produced from finger 4 is reflected back through the light transmitting substrate 2 and volume hologram 3 and is collected by image detection system 8 which is substantially aligned along optical axis 99. Notably, however, if a more compact or convenient geometry is desired in any particular application, optical axis 99 of the image detection system hereof may be bent by arranging optical elements (e.g. mirrors) between the light transmitting substrate 2 and image detector 7b.

Although modified somewhat by the slant angle of its fringes, the volume hologram 3 of the illustrative embodiments has filtering properties similar to standard reflection-type volume holograms having fringes aligned parallel to the recording medium. Consequently, the spectral wavelength of light rays diffracted from volume hologram 3 are within a narrow wavelength bandwidth along a portion of the electromagnetic spectrum. Samples of the slanted-fringe hologram shown in FIG. 2 were made using the 514.5 nm spectral line of an Argon laser, and due to processing and material properties, the emitted light was shifted and measured to have a center wavelength of 528 nanometers(nm) and a full-width half maximum wavelength bandwidth of 11 nanometers. Thus, since the volume hologram used in the system of the illustrative embodiments of the present invention is a self-filtering device, illuminating light source 1 can be realized as a white light source, such as a tungsten halogen lamp. Alternatively, the light source can be realized by a more monochromatic source, such as an LED, or a laser matched to the emission wavelength of the hologram or tuned to a slightly different angle than the one used to construct the hologram (and thus match the Bragg condition for the particular fringe slant of the hologram). Also, since the substrate edge of the light transmitting substrate is typically long and thin, thus requires an anamorphic beam shape for optimal light entry efficiency, the illuminating beam may be reshaped with lenses, such as a combination of spherical and/or cylindrical lenses, to make more efficient use of the available light.

Preferably, light transmitting substrate 2 has an index of refraction which closely matches the index of refraction of volume hologram 3. The index of refraction of substrate 2 should typically be equal to or less than the index of refraction of volume hologram 3. When recording the slanted-fringe light diffractive grating within the volume hologram, the index matching criteria is particularly important to achieve high diffraction efficiency, and fringe contrast. These properties can be achieved by satisfying the following condition: the thinner the substrate, or the steeper the angle of travel of the light beam within the substrate, the closer the index of refraction of the substrate and the holographic recording material must match.

Referring now to FIGS. 3 and 4, the second and third illustrative embodiments of the image detection device of the present invention will be described. These devices of these illustrative embodiments are similar to the device of the first illustrative embodiment, expect for the geometry of the light transmitting substrate and the manner in which illuminating light is coupled thereinto. While FIGS. 3 and 4 show two possible alternative substrate geometries, it is understood that those skilled in the art of optical design will readily derive other ways of injecting light into the substrate so that it travels though the light transmitting substrate and strikes the affixed slanted light diffractive grating at an oblique angle, as shown in FIG. 2.

As shown in FIG. 3, the image detection device of the second illustrative embodiment utilizes a face-lit light input coupling technique. Typically, this technique requires that the light transmitting substrate 21 be slightly longer along its longitudinal extent. As shown, light emitted from light source 20 and conditioned by optional light conditioning optics first passes through substrate 21 and impinges on reflection-type hologram 22 embodying a slanted light diffractive grating. This volume hologram 22 is laminated or otherwise attached to substrate 21 and has an index of refraction that closely matches that of substrate 21 as noted above. If desired, hologram 22 may contain a mirrored backing to enhance the amount of light which travels into substrate 21, or an absorptive backing to minimize stray light, or no backing at all.

As shown in FIG. 3, light is diffracted by volume hologram 22 (i.e. input light coupling element) at an angle greater than the critical angle for the substrate 21 and travels within substrate 21 to directly strike the slanted light diffractive grating prerecorded in reflection-type volume hologram 23, as described in the first illustrative embodiment. First order diffracted light 25 produced by hologram 23 passes through light transmitting substrate 21 along optical axis 99 to produce aforementioned glare field which is interrupted by the ridges of finger 24 placed on the object illuminating region of the light transmitting substrate. The fingerprint image produced from finger 24 passes through substrate 21, through hologram 23 and to image detection system 28, which comprises an objective lens 26 and an electronic image detector 27. In the illustrative embodiment of FIG. 3, light used to illuminate volume hologram 23, does not undergo total internal reflection within the substrate 21 before illuminating volume hologram 23.

In FIG. 4, a third illustrative embodiment of the image detection device of the present invention is shown. Unlike the second embodiment, the third illustrative embodiment utilizes the principles of total internal reflection to deliver the light beam to the object to be illuminated. Such light guiding techniques are disclosed in U.S. Pat. No. 5,295,208 to Caulfield, et al, incorporated herein by reference. As shown in FIG. 4, light produced from light source 10 and conditioned by light conditioning optics impinges upon the slanted light diffracted grating embodied in transmission-type hologram 11 which is laminated or otherwise attached to light transmitting substrate 12. This incident light is diffracted into substrate 12 at an angle greater than the critical angle for substrate 12. Consequently, the light bounces off the opposing surface by total internal reflection within substrate 12 and travels within substrate 12 to strike a slanted fringe light diffractive grating embodied within reflection-type hologram 13. The light falling at the correct angles on volume hologram 13 is diffracted thereby and travels through substrate 12 to form beam 15 whose reflection produces an glare field. The glare field is interrupted by finger 14 placed on the illuminating region of the light transmitting substrate 12. The fingerprint image produced from finger 14 passes through substrate 12 and through volume hologram 13 and is collected by an image detection system 18 comprising a lens 16 or other means (e.g. micro-channel plate or micro-lens array) transfers the fingerprint image to the image detection plane of an image detector 17.

Figure 5:
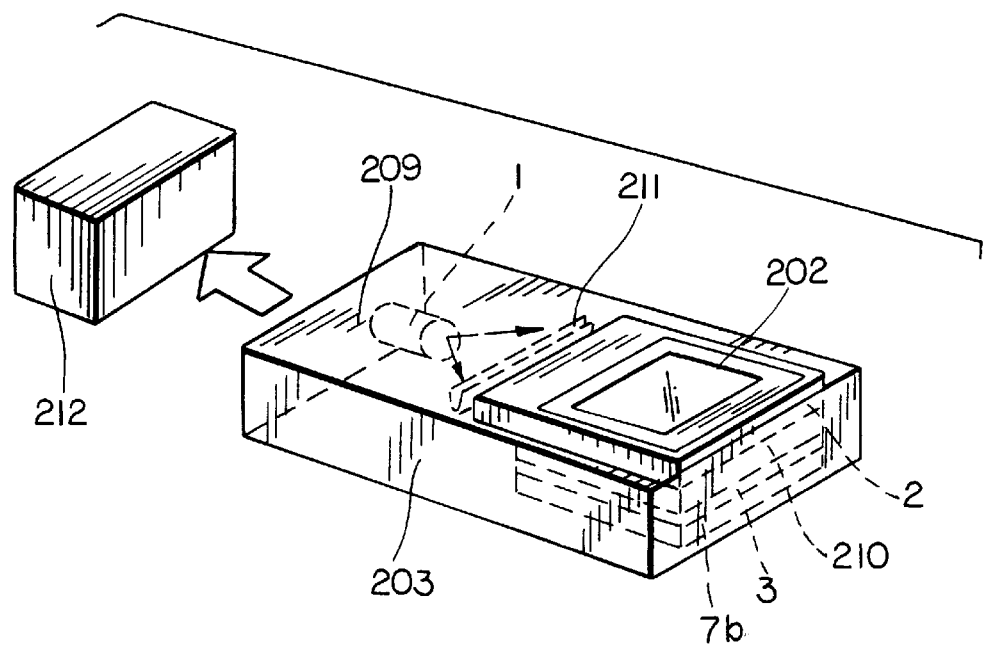
FIG. 5 is a perspective view of the topographical image detector of the fourth illustrative embodiment of the present invention, in which substantially monochromatic light and a reflection-type volume hologram embodying a slanted-fringe light diffractive grating are used to illuminate the object illuminating region of the light transmitting substrate, while a CCD image detector affixed to the light transmitting substrate is used to detect the image of the topographical pattern of the illuminated object positioned along the optical axis of the CCD image detector.
Figure 5A:
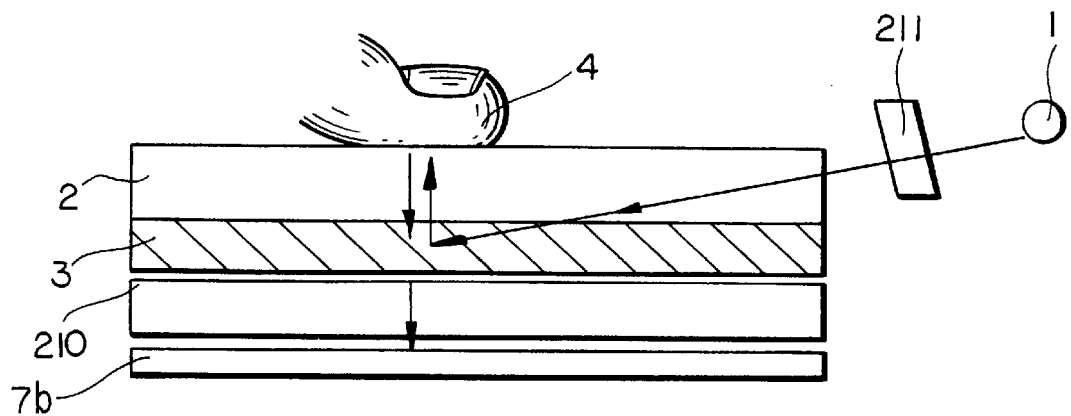
FIG. 5A is a cross-sectional view of the topographical image detector of FIG. 5.

In FIGS. 5 and 5A, the fourth illustrative embodiment of the image detection device is shown in the form of an extremely thin, compact device adapted for use with the system shown in FIG. 1. This embodiment of the present invention is particularly suited for use in access control devices incorporated within portable computers, associated PCMCIA cards, cellular telephones, or other devices where minimal space for fingerprint verification device is available.

As shown in FIGS. 5 and 5A, the fourth illustrative of the image detection device comprises a number of subcomponents compactly integrated within the interior of an ultra compact housing about the size of a PCMCIA package. As shown such components include: light transmitting substrate 2 having a finger illuminating region; a reflection-type volume hologram 3 affixed to the underside of substrate 2, and having a slanted-fringe light diffractive grating embodied therein; and a first narrow band-pass filter panel 210 directly affixed to the underside of the volume hologram 3 and tuned to the output wavelength of volume hologram 3; a CCD image detection panel 7B directly affixed to the underside of the narrow band-pass filter by way of an adhesive or index matching layer. As shown, each of these optical components is aligned with optical axis 99. The device also includes a substantially monochromatic light source 1 and optional beam shaping optics, for producing a substantially monochromatic light beam tuned in wavelength or input angle to match the Bragg angle condition for grating or hologram 3. Alternatively, a white light source may be used instead of a laser. In such a case, the white light beam is passed through a second narrow band-pass filter 211 selected as above in order to match the Bragg condition for the slanted fringe light diffractive grating embodied within the volume hologram 3. Notably, narrow band-pass filter 210 eliminates stray light or unwanted fluorescence from the finger by virtue of its narrow pass band. Electronic I/O circuitry 212 is provided for powering the light source 1 and image detector 7b and passing information to and from image detector 7b. Such circuitry may be interfaced to an appropriate connector, or connectors, located, for example, on edge 209 of housing 203. Preferably, the entire structure is housed in compact housing 203. During operation of this illustrative embodiment, the finger is placed through opening 202 in housing 203 onto planar finger illuminating region 204. The light transmitting substrate 2 and volume hologram affixed 3 thereto may comprise the protective cover plate required for CCD image detector 7b.

Figure 6:
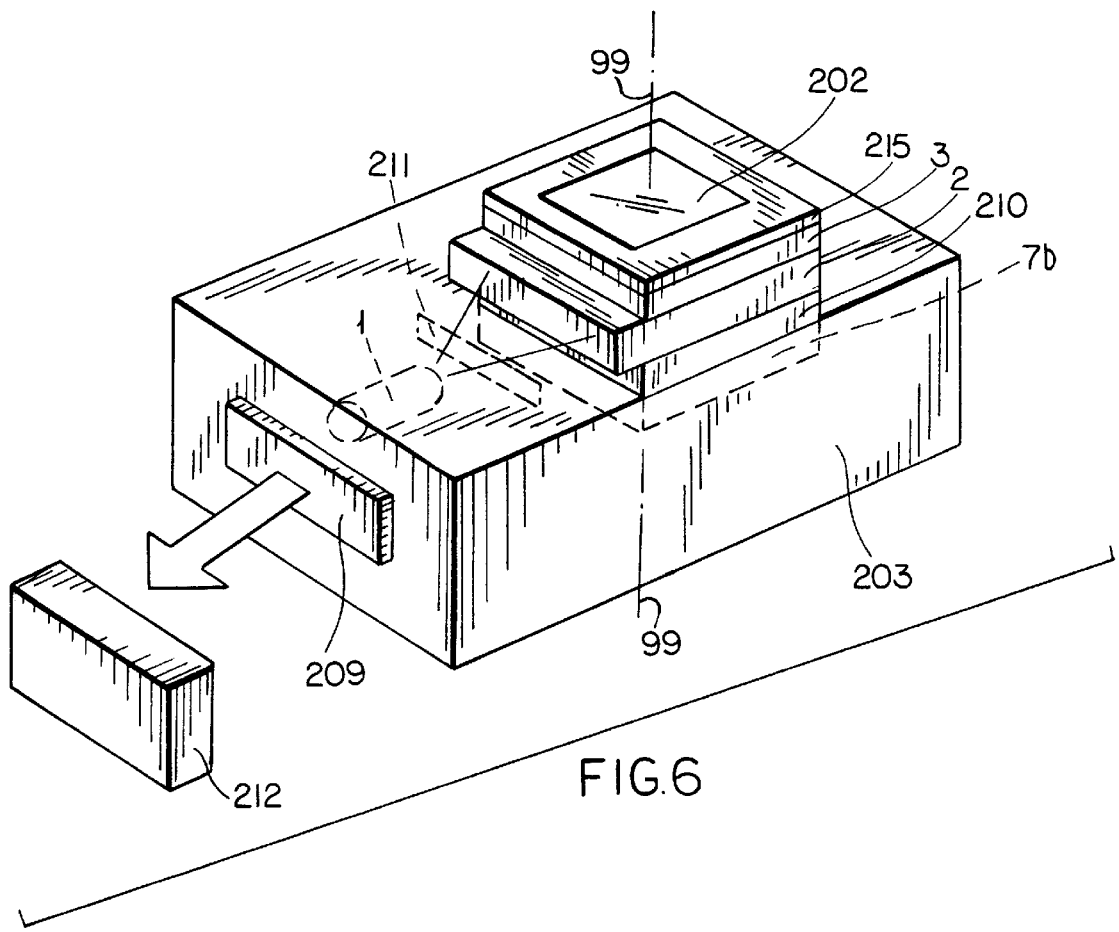
FIG. 6 is a perspective view of the topographical image detector of the fifth illustrative embodiment of the present invention, in which substantially monochromatic light and a transmission-type volume hologram embodying a slanted-fringe light diffractive grating are used to illuminate the object illuminating region of the light transmitting substrate, while a CCD image detector affixed to the light transmitting substrate is used to detect the image of the topographical pattern of the illuminated object positioned along the optical axis of the CCD image detector.
Figure 6A:
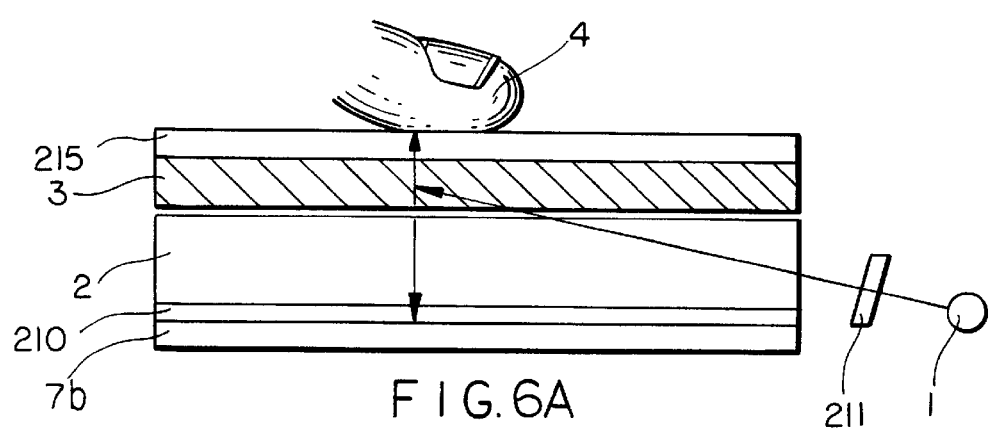
FIG. 6A is a cross-sectional view of the topographical image detector of FIG. 6.

As shown in FIGS. 6 and 6A, the fifth illustrative embodiment of the image detection device comprises a number of subcomponents also compactly integrated within the interior of an ultra compact housing about the size of a PCMCIA package. As shown such components include: a transmission-type volume hologram 3 having a slanted fringe light diffractive grating embodied therein; an optically transparent protective layer 215 affixed to the top surface of volume hologram 3 and serving to provide a finger supporting surface; a light transmitting substrate 2 affixed to the underside of the transmission-type volume hologram 3; a first narrow band-pass filter panel 210 approximate to, or directly affixed to the underside of the light transmitting substrate 2 and tuned to the output wavelength of volume hologram 3; a CCD image detection panel 7B proximate to, or directly affixed to the underside of the narrow band-pass filter by way of an adhesive or index matching layer. As shown, each of these optical components is aligned with optical axis 99. The device also includes a light source 1, and optional beam shaping optics, for producing a substantially monochromatic light beam tuned in wavelength or input angle to match the Bragg angle condition for transmission volume hologram 3. Alternatively, a white light source 1 may be used instead of a laser. In such a case, the white light beam is passed through a second narrow band-pass filter 211 selected as above in order to match the Bragg condition for the slanted fringe light diffractive grating embodied within the volume hologram 3. The function of narrow band-pass filter 210 is to eliminate stray light or unwanted fluorescence from the finger by virtue of its narrow pass band. Electronics circuitry 212 is also provided for powering the light source 1 and image detector 7b and passing information to and from image detector 7b. Such electronic circuitry may be interfaced to an appropriate connector, or connectors, located, for example, on edge 209 of housing 203. Preferably, the entire structure is housed in compact housing 203, as in the fourth illustrative embodiment. During operation of this illustrative embodiment, the finger of a subject to be identified is placed through opening 202 in housing 203 onto planar finger illuminating region 204. Notably, as shown, in this illustrative embodiment, transmission volume hologram is illuminated by light passing through the light transmitting substrate 2 into the transmission hologram 3.

In the fifth illustrative embodiment of FIGS. 6 and 6A, the fringe slant angle of the transmission hologram is generally such that the optical axis of the diffracted beam travels at angle less than the critical angle of the substrate and/or recording medium. The function and properties of such a slanted fringe transmission grating are similar to that of a reflection-type light diffractive grating. As such, this alternate embodiment of the image detection system of the present invention will operate in a similar fashion to the system configuration shown in FIG. 2.

Notably, a principal advantage of the image detection device shown in FIG. 5 through 6A is that no image transfer means is utilized, permit an ultra-compact construction.

Figure 7:
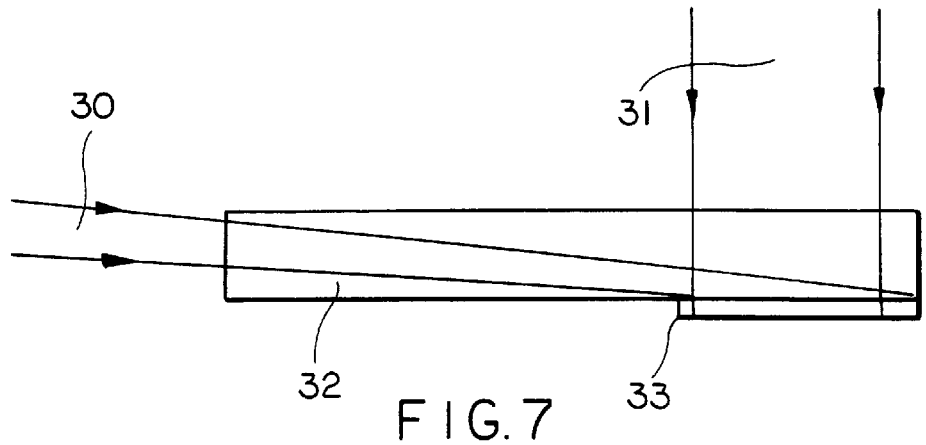
FIG. 7 shows an optical arrangement for recording slanted-fringe light diffractive gratings within transmission-type volume holograms used in the construction of topographical image detectors of the present invention.
Figure 8:
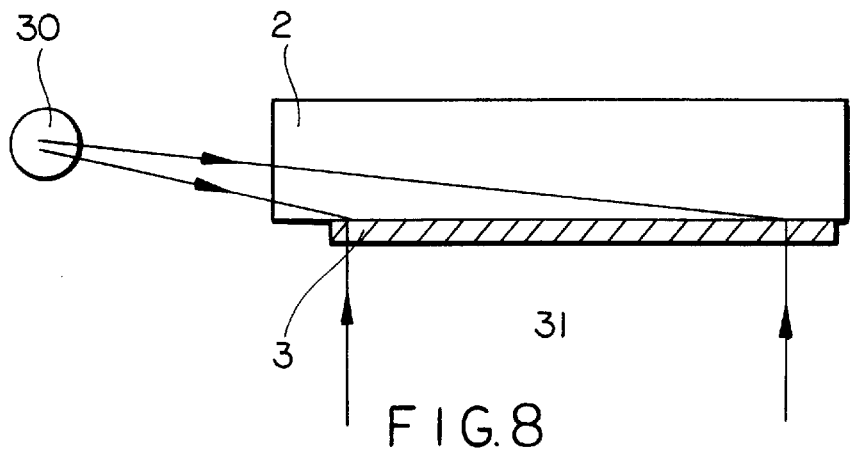
FIG. 8 shows an optical arrangement for recording slanted-fringe light diffractive gratings within reflection-type volume holograms used in the construction of topographical image detectors of the present invention.
Figure 9:
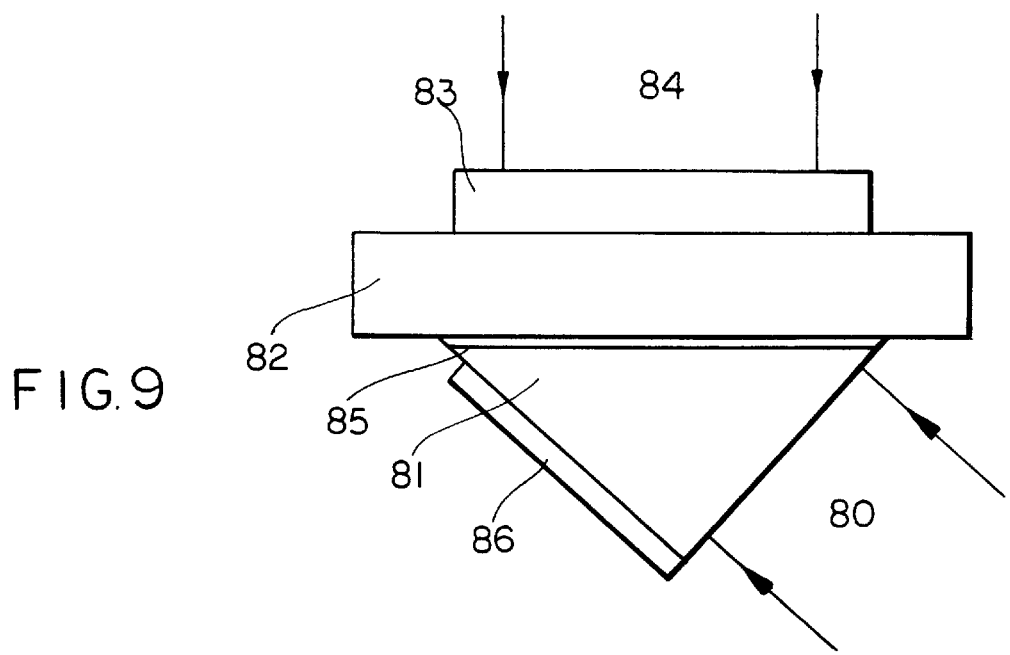
FIG. 9 shows an alternative optical arrangement for recording slanted-fringe light diffractive gratings within reflection-type volume holograms used in the construction of topographical image detectors of the present invention.

The following holographic recording method has been successfully practiced during the production of both light transmission and reflection holographic structures embodying slanted-fringe light diffractive gratings that have been incorporated into topographic image detection systems of the first through five illustrative embodiments of the present invention. Notably, the slanted fringe light diffractive gratings used in such devices will produce substantially collimated light rays for object illumination. The optical recording arrangements shown in FIGS. 7 through 9 are configured for producing such types of slanted fringe light diffractive gratings. However, as will be shown hereinafter with reference to FIGS. 11 through 13, it is possible to use slanted gratings that produce light rays that converge from a perspective point, as in the case of viewing objects with human vision. While reference is made to the optical recording arrangements of FIGS. 7 to 9 in the below described method, it is understood that the method is equally applicable to the production of the slanted gratings used in the sixth, seventh and eighth embodiments of the present invention shown in FIGS. 11 through 13. However, in such embodiments, the optical recording arrangements shown in corresponding FIGS. 11A and 12A would be used.

When recording the slanted-fringe light diffractive grating within the hologram 3, it is particularly important to achieve high diffraction efficiency, and high fringe contrast. It has been discovered that this can be achieved by closely matching the index of refraction of the light transmitting substrate 2 with the index of refraction of the recording medium used to make the volume hologram 3 in the illustrative embodiments. In general, there are two different cases to consider. As will be described below, each case has its own special approach to index matching.

Figure 10:
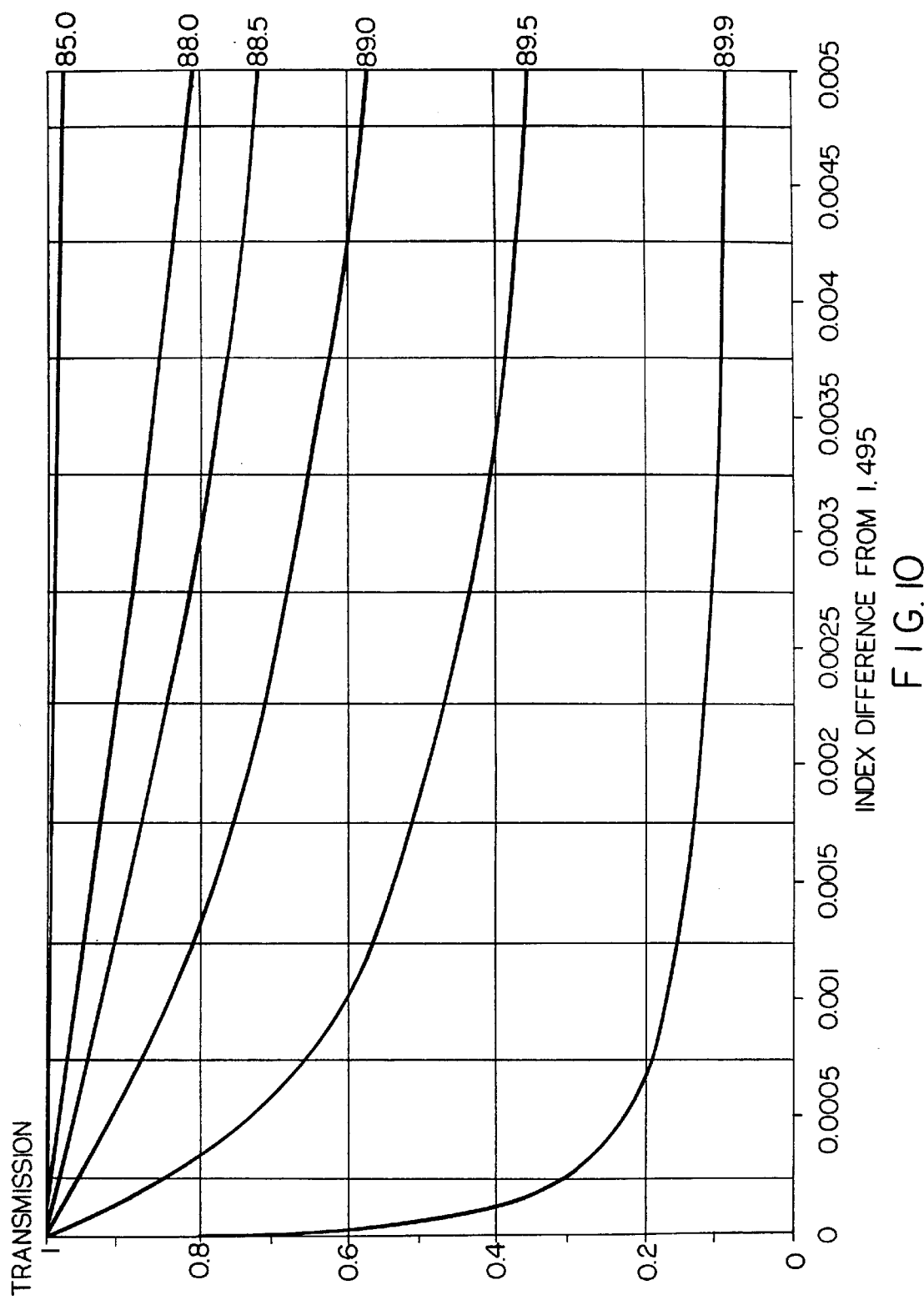
FIG. 10 shows an exemplary "light transmission versus index difference" graph which can be used to match the index of refraction of the substrate to the index of refraction of the recording medium during the manufacture of volume holograms used in the topographical image detectors of the present invention.

In the first case, where the index of refraction of substrate 2 is equal to or less than the index of refraction of recording medium 3, the above-described properties can be achieved by satisfying the following condition: the thinner the substrate, or the steeper the angle of travel of the light within the substrate, the closer the index of refraction of the substrate and the recording material must match. The graph of FIG. 10 illustrates the importance of the above-described index matching criterion. The set of curves associated with this graph shows the percentage of s-polarized light which will be transmitted from a substrate having an index of refraction less than 1.495 by the amount shown on the x-axis into a recording medium having an index of refraction of 1.495. Each curve represents the angle of incidence of a light wave within the substrate, as measured to the normal to the substrate. In order to achieve a compact, cost-effective system, it is desirable to utilize thin substrates, necessitating incident angles within the substrate approaching 90 degrees. FIG. 10 shows curves for arbitrarily selected steep incident angles of 85, 88, 88.5, 89, 89.5 and 89.9 degrees. These curves were derived from the well known Fresnel reflection equations combined with the Snell's Law equation, as may be found, for example, in *Optics* by K. D. Moller, University science Books, Mill Valley, Calif., 1988, page 196. The values shown on the x-axis were arbitrarily selected to extend to 0.005, representing a refractive index of 1.490 for the substrate. It should be understood that the values indicated in FIG. 10 were arbitrarily selected for illustration purposes, and do not represent specific physical bounding values. As can be seen from this graph, significant transmission of light into the recording medium from a thin substrate can be achieved by closely matching the index of refraction of the substrate and recording medium. For a particular grazing angle of incidence for the reference beam during recording (or reconstruction beam on playback), the graph of FIG. 10 shows how close the match must be. Clearly, the index match is functionally dependent on the incident angle of the laser beam used to record the slanted light diffractive grating.

In the second case, where the index of refraction of the recording medium is less than the index of refraction of the substrate, an evanescent wave is naturally produced at the boundary between the substrate and the recording medium. This results in limited penetration of the light beam from the substrate into the volume of the recording medium. If certain recording media are used (e.g. the DuPont family of holographic photopolymers having migratable monomer components drawn towards light), then the creation of an evanescent wave at the boundary between the recording medium and the substrate, will draw monomer to the boundary between the substrate and the recording layer. This monomer migration process increases the local index of refraction, thereby allowing the holographic recording reference beam to penetrate into the volume of the recording medium. This self-induced index matching effect enables interference of the reference beam with an object beam so as to produce recordable and permanent high-contrast slanted fringes within the recording medium. Thus when the recording medium index of refraction is slightly less than the index of refraction of the substrate, it is nevertheless possible to achieve sufficient index matching and recording of high fringe contrast in slanted light diffractive gratings.

Having addressed index matching requirements, the holographic recording procedure will now be described in detail below. The first step of the holographic recording procedure hereof involves cutting a piece of DuPont holographic recording film material (designated HRF 352 having index of refraction at the sodium D line of approximately 1.506) into a 2 inch square. Then using a roller pressure technique, the square is laminated to a piece of BK10 glass whose edges were polished to an optical finish. Notably, these materials are index matched in accordance with the above-described method. The resulting structure, having approximately a half inch thickness and an index of refraction at the sodium D line of 1.498, was used as the recording substrate. Using the optical arrangement shown in FIG. 8, the film material was exposed to Argon laser light at 514.5 nm using s polarization and other well known and standard holographic recording techniques. The angle of incidence of the reference beam within the glass substrate, was approximately 88 degrees. The film was exposed to approximately 500 mJ/cm$^2$. The details of the recording arrangement are described below in connection with the recording of reflection holograms.

As shown in FIG. 8, the reference beam 30, which may be collimated, converging or diverging, or otherwise anamorphically shaped, depending on the application and how the reconstruction illumination is to be shaped, is fed through the edge of substrate 2. Alternatively, the reference beam may also be fed from the face as discussed previously. The reference beam then travels within the substrate and impinges on holographic photosensitive medium 3 laminated to substrate 2. The object beam, 31, while depicted in FIG. 2 as being collimated, may be converging or diverging, depending on the application. This beam 31 impinges on holographic recording medium 3 with an optical axis, such that the reconstructed first order diffraction beam will travel at an angle with respect to optical axis 99 about or less than the critical angle for the substrate and/or recording medium, as shown. The side that the object beam strikes holographic recording medium 3 depends on the final application, and determines whether the hologram will be transmission hologram (as shown in FIG. 7) or a reflection hologram (as FIG. 8). The interference of the two beams within the volume of the holographic recording medium 3 expose the same.

If the diffracted illumination beam used to illuminate the object has insufficient uniformity, there are various techniques that may be used to precompensate the exposure of the hologram to achieve uniform reconstruction illumination. One such method includes using a mask with varying transmission which may be photographically or vacuum coated or otherwise produced which is placed before exposure of the hologram in the object beam and/or the reference beam to precompensate the exposure densities and thus fringe contrast in the recorded hologram to take into account the unevenness of the reconstruction illumination and thus yield a reconstructed diffraction illumination light field emitted from the hologram which is uniform in intensity and will thus uniformly illuminate the object under test.

During development of the holographic light diffractive grating, the exposed film structure may be left on the glass substrate and then processed with ultraviolet light and an optional heat cure, as prescribed by DuPont. However, for convenience, the exposed film structure was peeled off the glass substrate and relaminated to an acrylic substrate having a ⅛ inch thickness and an index of refraction of approximately 1.491. Thereafter, the exposed film structure can be UV cured in order to permanently fix the interference fringes within the film structure. Notably, the reason why the acrylic substrate is preferred during playback, is that is more cost effective and, unlike glass, is not prone to breakage. Since the close index matching noted above is most important during recording of the hologram, the index differential of the acrylic substrate merely serves to shift the angle of incidence somewhat of the illuminating beam. However, as shown in FIG. 10, the acrylic substrate does not transmit the reconstructed light as efficiently as a closely matched substrate otherwise would.

Alternatively, one may use an intermediate index matching medium (e.g. fluid, glue or other adhesive) disposed between the light transmitting substrate and the holographic recording medium. Also, the holographic recording medium may be coated onto the light transmitting substrate using, for example, dip or spin coating techniques. In such instances, the index of refraction of the intermediate coupling medium should preferably be equal to the index of refraction of the light transmitting substrate 2, or the slanted grating optical element 3, or have an index of refraction between the index of refraction of the substrate 2 and the slanted grating optical element 3.

FIG. 9 shows an additional way of making the above referred to holograms. This general technique of making "total internal reflection holograms" is described, for example, by Stetson in Optik, Volume 29, at pages 520–537 (1969). The method shown in FIG. 9 is modified and improved over that described by Stetson in because substrate 82 closely matches the index of refraction of the holographic medium 83 as noted above. In this optical recording arrangement, laser light is split into an object beam and a reference beam as is commonly done in the holographic art. Reference beam 80 impinges on prism 81 which is coupled to substrate 82 by way of an index matching fluid 85, whose index of refraction is desirably equal to the index of refraction of the substrate 82, or the prism 81, or somewhere in between those indices. A light absorber 86 is attached to the prism 81, as shown. Photosensitive holographic medium 83 is laminated or otherwise index matched or attached to substrate 82. Substrate 82 closely matches the refractive index of holographic medium 83 as noted above, and if any index matching or other attaching means is used between the substrate 82 and the holographic recording medium 83, its index of refraction must equal that of substrate 82 or holographic medium 83 or be somewhere in between those values. Object beam 84 strikes the holographic medium approximately perpendicular to it. The interference of the object beam and the reference beam cause slanted fringes to be formed within the holographic medium. The medium is then disattached from the prism and processed using known holographic recording medium processing techniques. The processed hologram is then laminated or otherwise attached to the light transmitting substrate 2 of the fingerprint imaging device of the present invention.

Oftentimes, it will be desirable to shape the wavefront of the (reconstruction) illumination beam with optics to match the wavefront used for the recording (reference) beam. This will minimize aberrations in the emitted first order beam, which is the conjugate of the original object beam. In some applications requiring extreme precision of measurement, minimizing these aberrations may be an important consideration. For applications with looser object illumination requirements, illumination with a more convenient wavefront, such as a spherical wavefront emanating from a small filament white light lamp, may produce perfectly satisfactory results.

In the topographic image detectors described above, the object (e.g. a finger) is illuminated using substantially collimated light rays produced from the slanted-fringe light diffractive gratings embodied in either the reflection or transmission volume holograms employed therein. Consequently, the size of the image detector 7B needs to be the same size as the illuminated object area to be viewed. In FIG. 11, there is shown a sixth illustrative embodiment which is particularly useful when desiring to view an illuminated object, such as finger, using ones eyes. As shown in FIG. 11, the topographical image detector includes a reflection type hologram 3 mounted to light transmitting substrate 2 with a finger supporting region. The hologram embodies a light diffractive grating which causes modulated light from the illuminated object, to converge to a perspective point (e.g. the pupil of the viewer's eye) so that he or she may easily view the image therefrom, as shown. This configuration may also be used to detect images on a smaller image detector placed at the focal point of the light diffractive grating.

In FIG. 11A, an optical recording arrangement is shown for making the reflection hologram used in the device of FIG. 11. In all other respects, the general method hereof can be followed to produce this type of light diffractive grating. As shown in FIG. 11A, an object beam 300 is passed through a large low f-number lens 308, to illuminate holographic recording medium 3 with a converging light beam 301 which passes through the recording medium 3 and substrate 3 and converges to a point several inches below the substrate. The portion of the beam 301 within the recording medium 3 must be larger in diameter than the object desired to later be illuminated. The reference beam 302 enters the substrate 2 and interfering with the object beam 301 forms a slanted fringe grating within the recording medium. The object and reference beams are preferably s-polarized. Index matching of the substrate to the recording medium is carried out as described above. Similarly, the relamination and reillumination techniques described above may also be practiced.

During operation of the image detection device of FIG. 11, a reconstruction beam is transmitted through substrate 2 which causes converging beam to be emitted from the hologram, illuminating the finger 4. A reflected converging light field, modulated by the topographic pattern of a fingerprint, is then reflected towards the image detector, in this case the viewers eye 303. The entire illuminated fingerprint is can be see by the naked eye of the viewer, or using a magnifying lens if desired for closer inspection.

In the sixth illustrative embodiment shown in FIG. 11, the reconstruction of the hologram produces what is known as the virtual image. Another possibility shown in FIG. 12 is to reconstruct the hologram with the conjugate of the original reference beam, which strikes the hologram from the opposite direction, 180 degrees from the original reference beam direction.

In FIG. 12, a seventh illustrative embodiment of the image detector of the present invention is shown. This embodiment uses phase conjugate reconstruction during its operation. As shown in optical recording arrangement of FIG. 12A, the object beam 330, shown as a collimated light beam, strikes the recording medium 3 such that the reconstructed first order diffracted light beam will have an angle with respect to optical axis 99, which is less than the critical angle for the substrate and/or recording medium. Reference beam 331 enters and travels through light transmitting substrate 2 at an oblique angle, and then enters recording medium 3 in order to interfere with object beam 330, causing the formation of a slanted fringe grating within the recording medium. The criteria for index matching the substrate to the recording medium, substrate material selection, the use of s-polarized light and other recording features described hereinabove apply to the making of the seventh illustrative embodiment shown in FIG. 12A. After the hologram is processed, a replay substrate 332 having characteristics matching those of other replay superstrate described herein, is laminated, indexed matched or otherwise affixed to the opposite side of the recording medium, as shown in FIG. 12. Light directing substrate 2 is then affixed to the underside of the hologram 3, and a narrow band pass filter 333 is affixed to the underside of substrate 3, as shown. A CCD image detector 334 is then affixed to the underside surface of the narrow band pass filter 333 to complete the construction of the image detection device of the seventh illustrative embodiment. Optionally, substrate 2 can be eliminated from the device in order to achieve a thinner resulting geometry, as this optical element is not required for the phase conjugate replay geometry of this illustrative embodiment.

During operation of the image detection device of FIG. 12, reconstruction illumination light 336 travels through replay superstrate 332 in the direction approximately 180 degrees opposite the direction of the original reference beam. This causes the hologram to reconstruct the object beam, which illuminates finger 4. The modulated reflected light from the finger 4 then travels; through the substrate 2 to the image detector 334.

In FIG. 13, an eighth illustrative embodiment of the image detection device of the present invention is illustrated. As shown, this embodiment comprises: a index discontinuity layer 320 disposed between a finger supporting layer 321 and reflection-type volume hologram 3; light transmitting substrate 2 affixed to hologram 3 with proper index matching requirements satisfied; a narrow band-pass filter 333 proximate to or affixed to the underside surface of substrate 2; and CCD image detection panel 334 affixed to narrow band-pass filter 333, as shown. The source of illumination 335 is arranged to enter through light transmitting substrate 2, from the opposite edge (i.e. transmission direction). The index discontinuity layer 320 should have an index of refraction low enough to cause total internal reflection of the illumination beam at the interface between layer 320 and light diffractive substrate 3. Layer 320, if not air, should also cause a reasonable index match to the protective layer 322 in order to avoid the formation of unwanted Moiré fringes.

During operation, the illuminating beam passes from source 335 into substrate 2 and through reflection-type volume hologram 3, where it is reflected at the interface between hologram 3 and index discontinuity layer 320 (e.g. realized as an air gap or partial index matching medium). As shown in FIG. 13, the illumination beam is then reflected back into volume hologram 3 at the correct angle as the phase conjugate of the original reference beam, thus satisfying the Bragg condition. This causes the hologram to transmit a beam substantially perpendicular to the plane of the hologram which then passes through index discontinuity layer 320, protective cover layer 321, to illuminate finger 4 supported thereon. Reflected light modulated by the illuminated finger pattern is then reflected back through optical elements 320, 3, 2 and 333 onto CCD image detection panel 334.

Figure 14:
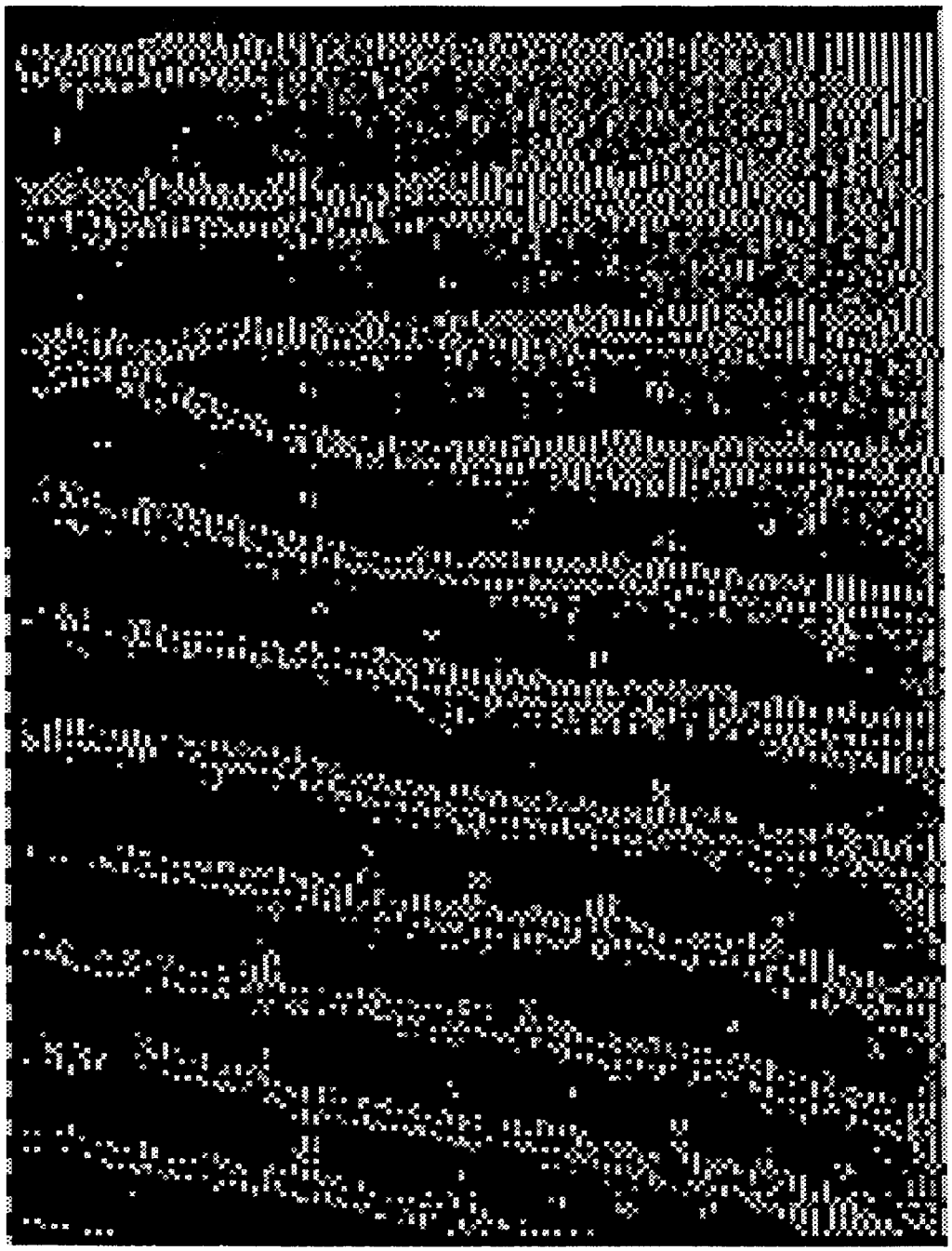
FIG. 14 is a graphical image of a fingerprint pattern detected by the topographical image detection system shown in FIGS. 5 and 5A.

FIG. 14 shows a frame-grabbed fingerprint image produced using the image detection system of the present invention. As shown, finger ridges and valleys can easily be seen, as well as pores. In this case, a volume hologram was used to produce the illuminating light beam, whereas illuminating light source was an Argon laser tuned at 514.5 nm. The beam of the laser was expanded anamorphically before entering the light transmitting substrate. The image formed on the CCD image detection array was frame-grabbed and stored in a graphic format computer file.

Having described the illustrative embodiment of the present invention, several modifications readily come to mind.

The slanted-fringe light diffractive grating may be recorded within the volume hologram of the image detection device so that light emitted from a LED or laser diode may be used for reconstruction (i.e. illumination).

The slanted fringe light diffraction gratings used in the device of the present invention may be embodied in non-holographic structures, using non-holographic recording techniques. An alternative holographic technique may include making slanted fringe gratings by immersing the recording medium in a large tank filled with an index matching fluid. In this approach to fringe grating production, the index matching fluid replace the substrate 2, but is subject to the same index matching versus input angle requirements illustrated in FIG. 10 and described hereinabove While a number of different embodiments have been described above, it is understood that the elements of such embodiments may be combined in accordance with the principles of the present invention to provide yet additional embodiments of the present invention. It is understood that while further modifications of the present invention will occur to persons with ordinary skill in the art, all such modifications are deemed to be within the scope and spirit of the present invention defined by the appended claims to the present invention.

What is claimed is:

1. A device for producing an image of a fingerprint having ridges and valleys, said device comprising:

light producing means for producing light rays;

a light transmitting substrate capable of transmitting the light produced by said light producing means;

a fingerprint illuminating region for physical placement of a finger bearing a fingerprint;

an image detection means for detecting an image of said fingerprint;

an optical element affixed to a portion of said light transmitting substrate and being disposed between said fingerprint illuminating region and said image detection means, said optical element embodying a light diffracting grating;

wherein said fingerprint illuminating region, said optical element and said image detection means are each disposed substantially along a common optical axis; and wherein during the operation of said device, (1) light rays produced by said light producing means, propagate within said light transmitting substrate towards said optical element and are diffracted by said light diffracting grating, (2) diffracted light rays produced by said light diffracting grating, propagate directly towards said fingerprint illuminating region and fall incident upon and are intensity modulated by the ridges and valleys of said fingerprint, and (3) intensity modulated light rays produced from said ridges and valleys propagate directly back through light transmitting substrate and said optical element and fall incident upon said image detection means, whereupon an image of said fingerprint is detected, said detected image including information corresponding to said ridges and valleys of said fingerprint.

2. The device of claim 1, wherein said light transmitting substrate has an upper surface in which said fingerprint illuminating region is disposed, and a lower surface arranged opposite said upper surface.

3. The device of claim 2, wherein said light diffracting grating comprises light diffracting structures that are slanted with respect to the upper and lower surfaces of said light transmitting substrate.

4. The device of claim 3, wherein said optical element is affixed to the lower surface of said light transmitting substrate.

5. The device of claim 4, wherein said light diffracting grating is a hologram containing a slanted fringe structure.

6. The device of claim 5, wherein said hologram is a volume hologram.

7. The device of claim 6, wherein said volume hologram is of the reflection type.

8. The device of claim 3, wherein said optical element is affixed to the upper surface of said light transmitting substrate, between said fingerprint illuminating region and said light transmitting substrate.

9. The device of claim 8, wherein said light diffracting grating is a hologram containing a slanted fringe structure.

10. The device of claim 9, wherein said hologram is a volume hologram.

11. The device of claim 10, wherein said volume hologram is of the transmission type.

12. The device of claim 8, which further comprises a light transmitting superstrate affixed to said upper surface of said optical element, and in which said fingerprint illuminating region is disposed.

13. The device of claim 12, wherein said light transmitting substrate, said optical element, said superstrate and said light producing means are contained within a compact housing having an access aperture through which said fingerprint can he placed in physical contact with said light transmitting superstrate, within said fingerprint illuminating region.

14. The device of claim 2, which further includes electronic circuitry for interfacing said image detection means with a computer-based system.

15. The device of claim 3, wherein said light transmitting substrate, said optical element and said light producing means are contained within a compact housing having an access aperture through which said fingerprint can be brought into physical contact with said light transmitting substrate, within said fingerprint illuminating region.

16. The device of claim 1, wherein said image detection means is an electro-optical image detector.

17. The device of claim 16, wherein said electro-optical image detector is an image detection array.

18. The device of claim 1, wherein said light producing means produces substantially monochromatic light.

19. The device of claim 1, wherein said light producing means comprises a white light source for producing white light.

20. The device of claim 19, which further comprises a narrow wavelength bandpass filter disposed between said white light source said light transmitting substrate.

21. The device of claim 1, which further comprises a narrow wavelength bandpass filter disposed substantially along said optical axis and between said optical element and said image detection means.

22. The device of claim 1, which comprises an image transfer means disposed between said image detection means and said optical element.

23. The device of claim 22, wherein said image transfer means is a structure selected from the group consisting of a lens system, a microchannel plate a fiber optic array, and a micro-lens array.

24. The device of claim 1, in combination with an image storage means for storing images produced by said image detection means.

25. The combination of claim 24, which further comprises an image analyzer and an image database.

26. The device of claim 1, wherein said light producing means is a structure selected from the group consisting of a monochromatic light source, a small filament incandescent lamp, and a light emitting diode.

27. The device of claim 1, wherein said light diffracting produces converging light rays when said light rays strike said light diffracting grating.

28. The device of claim 1, wherein said light diffracting grating produces substantially collimated light rays when said light beam strikes said light diffracting grating.

29. The device of claim 1, wherein said light diffracting grating produces diverging light rays when said light rays strike said light diffracting grating.

30. The device of claim 1, wherein the indices of refraction of said light transmitting substrate and said optical element are matched to optimize light transmission efficiency therebetween.

31. The device of claim 1, wherein light rays produced from said light producing means strike said light diffracting grating such that the first diffraction order of said diffracted light travels along said optical axis at an angle with respect to said optical axis, which is less than the critical angle for said light transmitting substrate.

32. The device of claim 1, wherein said fingerprint illuminating region is associated with a portion of said light transmitting substrate about said optical axis.

33. The device of claim 1, wherein said fingerprint illuminating region is associated with a portion of said optical element about said optical axis.

34. The device of claim 1, which further comprises a light transmitting substrate operably associated with said optical element.

35. The device of claim 1, which further comprises a PCMCIA-type housing containing said light producing means, said light transmitting substrate, said optical element, and said image detection means.

\* \* \* \* \*